United States Patent
Chen et al.

(10) Patent No.: US 10,501,431 B2
(45) Date of Patent: Dec. 10, 2019

(54) SELENIUM-ENRICHED TEA POLYPHENOL SELENIDE PREPARATION

(71) Applicant: Shanghai Ai Qi Ecological Technology Co., Ltd., Shanghai (CN)

(72) Inventors: Gong Chen, Shanghai (CN); Kunyuan Song, Shanghai (CN)

(73) Assignee: Shanghai Ai Qi Ecological Technology Co., Ltd., Shanghai (CN)

( * ) Notice: Subject to any disclaimer, the term of this patent is extended or adjusted under 35 U.S.C. 154(b) by 1547 days.

(21) Appl. No.: 14/361,301

(22) PCT Filed: Mar. 26, 2014

(86) PCT No.: PCT/CN2014/074095
§ 371 (c)(1),
(2) Date: May 29, 2014

(87) PCT Pub. No.: WO2015/131421
PCT Pub. Date: Sep. 11, 2015

(65) Prior Publication Data
US 2019/0144412 A1    May 16, 2019

(30) Foreign Application Priority Data
Mar. 6, 2014 (CN) .......................... 2014 1 0080979

(51) Int. Cl.
*C07D 311/62* (2006.01)
*C01B 19/00* (2006.01)
*A23L 33/105* (2016.01)
*A23L 33/16* (2016.01)

(52) U.S. Cl.
CPC .......... *C07D 311/62* (2013.01); *A23L 33/105* (2016.08); *A23L 33/16* (2016.08); *C01B 19/00* (2013.01); *A23V 2002/00* (2013.01)

(58) Field of Classification Search
CPC .................................................. C07D 311/62
USPC ......................................................... 549/399
See application file for complete search history.

(56) References Cited

PUBLICATIONS

Zhou, Fine Chem. (2007) vol. 3(24), pp. 248-251.*

* cited by examiner

*Primary Examiner* — Taofiq A Solola

(57) ABSTRACT

A selenium-enriched tea polyphenol selenide, has such a structure as

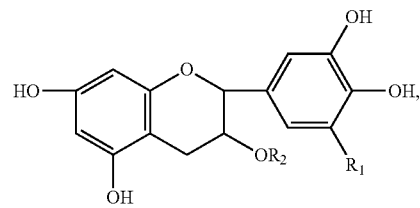

wherein $R_1$ is alkali metal ion and selenium coordination complex, and $R_2$=H, or

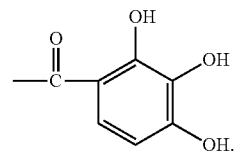

A method for preparing the selenium-enriched tea polyphenol selenide, comprises: A) reacting tea polyphenol with at least one inorganic metallic alkali, to obtain tea polyphenol hydroxy acid salt; and B) reacting the tea polyphenol hydroxy acid salt with $SeO_2$, to obtain the selenium-enriched tea polyphenol selenide.

8 Claims, 12 Drawing Sheets
(10 of 12 Drawing Sheet(s) Filed in Color)

| Sample Name: | 1 | Injection Volume: | 20.0 |
| --- | --- | --- | --- |
| Vial Number: | BB4 | Channel: | UV_VIS_1 |
| Sample Type: | unknown | Wavelength: | 275 |
| Control Program: | 2013 | Bandwidth: | n.a. |
| Quantif. Method: | 20100910 | Dilution Factor: | 1.0000 |
| Recording Time: | 2013-8-20 14:26 | Sample Weight: | 1.0000 |
| Run Time (min): | 60.00 | Sample Amount: | 1.0000 |

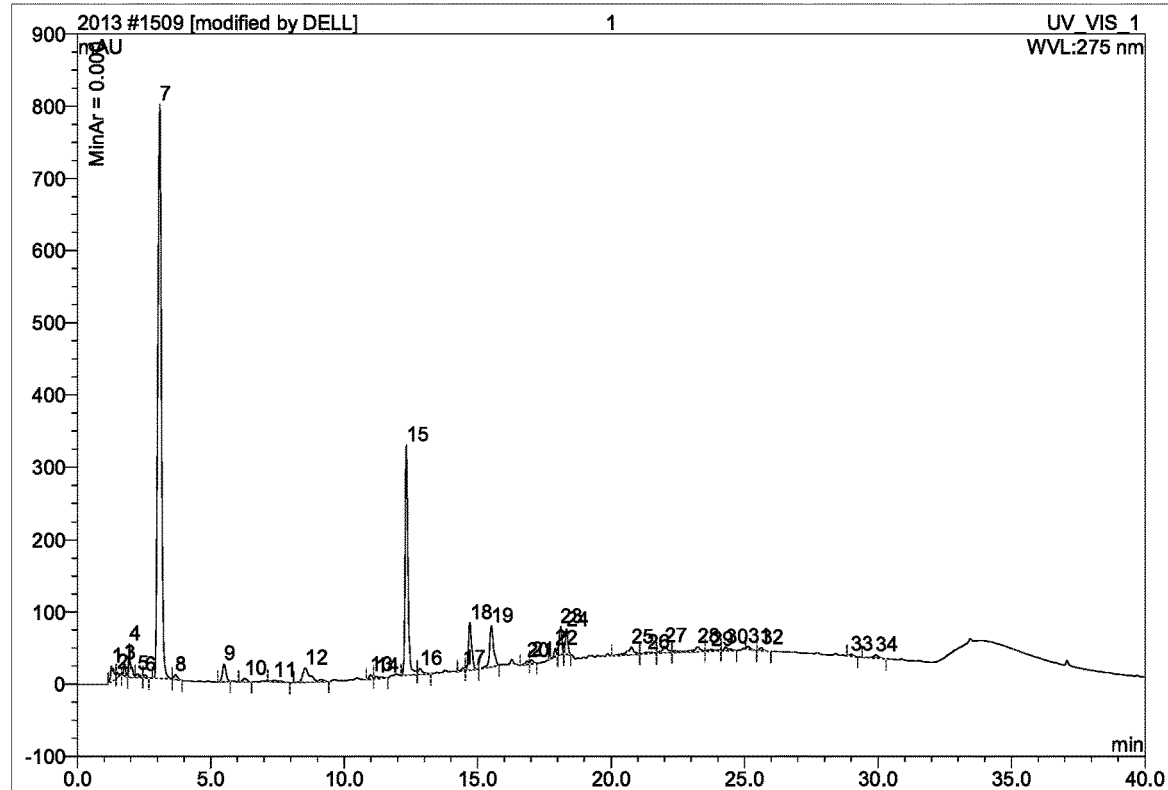

| No. | Ret.Time min | Peak Name | Height mAU | Area mAU*min | Rel.Area % | Amount | Type |
| --- | --- | --- | --- | --- | --- | --- | --- |
| 1 | 1.28 | n.a. | 21.720 | 2.954 | 1.24 | n.a. | BM |
| 2 | 1.50 | n.a. | 6.798 | 0.664 | 0.28 | n.a. | Mb* |
| 3 | 1.77 | n.a. | 17.440 | 1.463 | 0.61 | n.a. | bMb |
| 4 | 1.95 | n.a. | 46.509 | 4.603 | 1.93 | n.a. | bM |
| 5 | 2.27 | n.a. | 3.986 | 0.529 | 0.22 | n.a. | Rd |
| 6 | 2.55 | n.a. | 4.199 | 0.524 | 0.22 | n.a. | MB* |
| 7 | 3.08 | n.a. | 794.968 | 125.734 | 52.81 | n.a. | BMb* |
| 8 | 3.68 | n.a. | 6.631 | 1.006 | 0.42 | n.a. | bMB |
| 9 | 5.50 | n.a. | 24.298 | 3.725 | 1.56 | n.a. | BMB* |
| 10 | 6.27 | n.a. | 4.821 | 1.007 | 0.42 | n.a. | BMB* |
| 11 | 7.37 | n.a. | 1.636 | 0.741 | 0.31 | n.a. | BMB* |
| 12 | 8.55 | n.a. | 19.528 | 6.729 | 2.83 | n.a. | BMB* |
| 13 | 10.98 | n.a. | 5.778 | 0.828 | 0.35 | n.a. | BM * |
| 14 | 11.22 | n.a. | 3.265 | 0.862 | 0.36 | n.a. | MB* |
| 15 | 12.33 | n.a. | 318.277 | 41.009 | 17.22 | n.a. | BM * |

Fig. 1

| | | | | | | | |
|---|---|---|---|---|---|---|---|
| 16 | 12.85 | n.a. | 7.932 | 1.546 | 0.65 | n.a. | MB* |
| 17 | 14.45 | n.a. | 4.232 | 0.640 | 0.27 | n.a. | BM |
| 18 | 14.72 | n.a. | 66.151 | 9.324 | 3.92 | n.a. | Mb* |
| 19 | 15.52 | n.a. | 56.747 | 9.566 | 4.02 | n.a. | bMB* |
| 20 | 16.85 | n.a. | 4.922 | 0.712 | 0.30 | n.a. | BM * |
| 21 | 17.03 | n.a. | 5.061 | 0.747 | 0.31 | n.a. | MB |
| 22 | 17.92 | n.a. | 11.517 | 1.200 | 0.50 | n.a. | BMb |
| 23 | 18.10 | n.a. | 39.538 | 4.200 | 1.76 | n.a. | bMb |
| 24 | 18.33 | n.a. | 34.703 | 3.781 | 1.59 | n.a. | bMB* |
| 25 | 20.77 | n.a. | 10.671 | 3.258 | 1.37 | n.a. | BM * |
| 26 | 21.37 | n.a. | 1.838 | 0.636 | 0.27 | n.a. | Mb* |
| 27 | 22.02 | n.a. | 9.573 | 2.235 | 0.94 | n.a. | bM |
| 28 | 23.25 | n.a. | 7.068 | 2.988 | 1.25 | n.a. | M * |
| 29 | 23.75 | n.a. | 2.541 | 1.038 | 0.44 | n.a. | M |
| 30 | 24.30 | n.a. | 5.043 | 1.170 | 0.49 | n.a. | MB* |
| 31 | 25.13 | n.a. | 4.082 | 0.548 | 0.23 | n.a. | BMB* |
| 32 | 25.62 | n.a. | 4.179 | 0.691 | 0.29 | n.a. | BMB |
| 33 | 28.98 | n.a. | 2.732 | 0.496 | 0.21 | n.a. | BMB |
| 34 | 29.92 | n.a. | 4.241 | 0.936 | 0.39 | n.a. | BMB |
| Total: | | | 1562.624 | 238.093 | 100.00 | 0.000 | |

Fig. 1 (cont.)

Table 1. Dose design and animal dose groups

| Group | Dose (mg/kg diet) | Gender | Amount | Animal code |
|---|---|---|---|---|
| Dose group 1 | 1000 | ♂ | 5 | 1100-1104 |
| Dose group 2 | 1280 | ♂ | 5 | 1200-1204 |
| Dose group 3 | 1600 | ♂ | 5 | 1300-1304 |
| Dose group 4 | 2000 | ♂ | 5 | 1400-1404 |
| Dose group 5 | 2500 | ♂ | 5 | 1500-1504 |
| Dose group 6 | 3000 | ♂ | 5 | 1600-1604 |
| Dose group 7 | 4000 | ♂ | 5 | 1600-1604 |
| Dose group 8 | 4500 | ♂ | 5 | 1700-1704 |
| Dose group 1 | 1000 | ♀ | 5 | 2100-2104 |
| Dose group 2 | 1280 | ♀ | 5 | 2200-2204 |
| Dose group 3 | 1600 | ♀ | 5 | 2300-2304 |
| Dose group 4 | 2000 | ♀ | 5 | 2400-2404 |
| Dose group 5 | 2500 | ♀ | 5 | 2500-2504 |

Fig. 2

Table 2. Concentration of test sample

| Group | Dose (mg/kg bw) | Intragastric volume (mL/kg bw) | Sample concentration (mg/mL) | Sample weight (g) | Metered volume (mL) |
|---|---|---|---|---|---|
| Dose group 1 | 1000 | 10 | 100 | 4.00 | 40 |
| Dose group 2 | 1280 | 10 | 128 | 5.12 | 40 |
| Dose group 3 | 1600 | 10 | 160 | 6.40 | 40 |
| Dose group 4 | 2000 | 10 | 200 | 8.00 | 40 |
| Dose group 5 | 2500 | 10 | 250 | 10.00 | 40 |
| Dose group 6 | 3000 | 10 | 300 | 3.00 | 10 |
| Dose group 7 | 4000 | 10 | 400 | 4.00 | 10 |
| Dose group 8 | 4500 | 10 | 450 | 4.50 | 10 |

Fig. 3

Table 3. Code of animal anatomised as planned

| Group | Gender | Animal code |
|---|---|---|
| Dose group 1 | ♂ | 1100-1104 |
| Dose group 2 | ♂ | 1200-1204 |
| Dose group 3 | ♂ | 1300-1304 |
| Dose group 4 | ♂ | 1400, 1402 |
| Dose group 5 | ♂ | 1500, 1501, 1502, 1504 |
| Dose group 6 | ♂ | 1601, 1603 |
| Dose group 7 | ♂ | 1600 |
| Dose group 1 | ♀ | 2101-2104 |
| Dose group 2 | ♀ | 2201, 2202 |
| Dose group 3 | ♀ | 2301 |
| Dose group 4 | ♀ | 2404 |

Fig. 4

Attached table 1. Result table of clinical symptom

| Symptom | Number of animals having clinical symptom in every dose group | | | | | | | |
|---|---|---|---|---|---|---|---|---|
| | 1000mg/kg bw | 1280mg/kg bw | 1600mg/kg bw | 2000mg/kg bw | 2500mg/kg bw | 3000mg/kg bw | 4000mg/kg bw | 4500mg/kg bw |
| Slow movement | 0 | 0 | 1 | 1 | 0 | 0 | 2 | 1 |

Fig. 5

Attached table 2. Result table of animal death

| Gender | Dose (mg/kg bw) | Deaths/Total number | Death rate (%) |
|---|---|---|---|
| Male | 1000 | 0/5 | 0 |
| | 1280 | 0/5 | 0 |
| | 1600 | 0/5 | 0 |
| | 2000 | 3/5 | 60 |
| | 2500 | 1/5 | 20 |
| | 3000 | 3/5 | 60 |
| | 4000 | 4/5 | 80 |
| | 4500 | 5/5 | 100 |
| Female | 1000 | 0/5 | 0 |
| | 1280 | 3/5 | 60 |
| | 1600 | 4/5 | 80 |
| | 2000 | 4/5 | 80 |
| | 2500 | 5/5 | 100 |

Fig. 6

Attached table 3. Comparison table of animal weight when grouping

| Gender | Original code | Weight when grouping (g) | New code |
|---|---|---|---|
| Male | 100 | 176.11 | 1400 |
| Male | 101 | 216.21 | ~ |
| Male | 102 | 167.02 | 1100 |
| Male | 103 | 209.43 | 1204 |
| Male | 104 | 167.56 | 1300 |
| Male | 105 | 178.29 | 1301 |
| Male | 106 | 176.94 | 1101 |
| Male | 107 | 215.74 | ~ |
| Male | 108 | 167.12 | 1200 |
| Male | 109 | 189.23 | 1302 |
| Male | 110 | 193.65 | 1504 |
| Male | 111 | 190.83 | 1303 |
| Male | 112 | 172.06 | 1500 |
| Male | 113 | 190.83 | 1403 |
| Male | 114 | 177.78 | 1501 |
| Male | 115 | 206.33 | 1404 |
| Male | 116 | 202.24 | 1304 |
| Male | 117 | 181.67 | 1201 |
| Male | 118 | 178.96 | 1401 |
| Male | 119 | 184.95 | 1202 |
| Male | 120 | 190.38 | 1503 |
| Male | 121 | 190.43 | 1203 |
| Male | 122 | 187.06 | 1402 |
| Male | 123 | 193.63 | 1104 |
| Male | 124 | 183.34 | 1102 |
| Male | 125 | 185.23 | 1502 |
| Male | 126 | 192.58 | 1103 |

Note: "~" means that the animal is not used in this test.

Fig. 7

Attached table 3. (continued) Comparison table of animal weight when grouping

| Gender | Original code | Weight when grouping (g) | New code |
|---|---|---|---|
| Female | 200 | 152.76 | 2201 |
| Female | 201 | 145.78 | - |
| Female | 202 | 155.24 | 2402 |
| Female | 203 | 152.33 | 2300 |
| Female | 204 | 154.04 | 2501 |
| Female | 205 | 156.92 | 2503 |
| Female | 206 | 158.33 | 2304 |
| Female | 207 | 153.27 | 2401 |
| Female | 208 | 155.28 | 2502 |
| Female | 209 | 155.09 | 2302 |
| Female | 210 | 155.96 | 2103 |
| Female | 211 | 151.54 | 2400 |
| Female | 212 | 155.02 | 2202 |
| Female | 213 | 156.31 | 2203 |
| Female | 214 | 156.70 | 2303 |
| Female | 215 | 150.52 | 2300 |
| Female | 216 | 156.87 | 2403 |
| Female | 217 | 150.23 | 2200 |
| Female | 218 | 159.07 | 2504 |
| Female | 219 | 157.83 | 2104 |
| Female | 220 | 152.55 | 2101 |
| Female | 221 | 149.37 | 2100 |
| Female | 222 | 158.30 | 2204 |
| Female | 223 | 140.38 | - |
| Female | 224 | 154.36 | 2102 |
| Female | 225 | 158.96 | 2404 |
| Female | 226 | 152.95 | 2301 |

Note : "-" means that the animal is not used in this test.

Fig. 7 (cont.)

Attached table 4. Change table of animal weight          Unit: g

| Dose | Gender | Code | On the dosing day | On the 3rd day after dosing | On the 6th day after dosing | On the 9th day after dosing | On the 12th day after dosing | On the 14th day after dosing |
|---|---|---|---|---|---|---|---|---|
| 1000mg/kg bw | Male | 1100 | 167.02 | 195.38 | 208.63 | 229.86 | 246.11 | 259.87 |
| | Male | 1101 | 176.94 | 189.84 | 194.45 | 193.02 | 219.38 | 232.05 |
| | Male | 1102 | 183.34 | 190.35 | 205.84 | 233.17 | 254.39 | 260.61 |
| | Male | 1103 | 192.58 | 205.62 | 212.97 | 226.58 | 251.73 | 261.59 |
| | Male | 1104 | 193.63 | 203.72 | 215.43 | 239.98 | 256.25 | 258.91 |
| 1250mg/kg bw | Male | 1200 | 167.12 | 178.82 | 179.23 | 200.39 | 228.21 | 233.74 |
| | Male | 1201 | 181.67 | 197.83 | 201.92 | 203.21 | 218.82 | 231.92 |
| | Male | 1202 | 184.95 | 196.37 | 198.47 | 225.72 | 268.21 | 270.83 |
| | Male | 1203 | 190.43 | 194.35 | 208.42 | 227.18 | 245.98 | 247.32 |
| | Male | 1204 | 209.43 | 218.32 | 233.23 | 256.81 | 273.33 | 285.82 |
| 1600mg/kg bw | Male | 1300 | 167.36 | 172.89 | 186.94 | 197.49 | 208.40 | 212.77 |
| | Male | 1301 | 178.29 | 178.73 | 183.79 | 204.30 | 220.15 | 221.38 |
| | Male | 1302 | 189.23 | 205.46 | 211.32 | 232.51 | 250.21 | 257.21 |
| | Male | 1303 | 190.83 | 192.16 | 201.84 | 226.71 | 239.84 | 244.61 |
| | Male | 1304 | 202.24 | 211.42 | 210.25 | 229.17 | 249.03 | 266.78 |
| 2000mg/kg bw | Male | 1400 | 176.11 | 163.78 | 165.38 | 186.28 | 210.33 | 223.36 |
| | Male | 1401 | 178.96 | - | - | - | - | - |
| | Male | 1402 | 187.06 | 191.83 | 201.63 | 216.92 | 238.03 | 244.84 |
| | Male | 1403 | 190.83 | - | - | - | - | - |
| | Male | 1404 | 206.33 | - | - | - | - | - |
| 2500mg/kg bw | Male | 1500 | 172.06 | 166.11 | 170.28 | 179.61 | 207.37 | 214.35 |
| | Male | 1501 | 177.78 | 156.63 | 162.97 | 164.85 | 186.49 | 202.24 |
| | Male | 1502 | 185.29 | 175.04 | 178.27 | 173.51 | 205.96 | 212.83 |
| | Male | 1503 | 190.38 | - | - | - | - | - |
| | Male | 1504 | 191.65 | 191.20 | 184.97 | 190.38 | 199.34 | 200.84 |
| 3000mg/kg bw | Male | 1600 | 175.32 | - | - | - | - | - |
| | Male | 1601 | 178.25 | 175.56 | 178.56 | 193.78 | 219.91 | 234.03 |
| | Male | 1602 | 166.47 | - | - | - | - | - |
| | Male | 1603 | 176.35 | 161.82 | 164.32 | 175.78 | 188.37 | 186.65 |
| | Male | 1604 | 175.83 | - | - | - | - | - |
| 4000mg/kg bw | Male | 1680 | 174.25 | 154.76 | 144.24 | 136.52 | 163.15 | 176.94 |
| | Male | 1681 | 173.54 | - | - | - | - | - |
| | Male | 1682 | 171.12 | - | - | - | - | - |
| | Male | 1683 | 167.35 | - | - | - | - | - |
| | Male | 1684 | 189.13 | - | - | - | - | - |
| 4500mg/kg bw | Male | 1700 | 164.35 | - | - | - | - | - |
| | Male | 1701 | 164.72 | - | - | - | - | - |
| | Male | 1702 | 166.54 | - | - | - | - | - |
| | Male | 1703 | 167.13 | - | - | - | - | - |
| | Male | 1704 | 166.24 | - | - | - | - | - |

Note: "-" means that the animal has been dead.

Fig. 8

Attached table 4. (continued) Change table of animal weight     Unit: g

| Dose | Gender | Code | On the dosing day | On the 3rd day after dosing | On the 6th day after dosing | On the 9th day after dosing | On the 12th day after dosing | On the 14th day after dosing |
|---|---|---|---|---|---|---|---|---|
| 1000mg/kg bw | Female | 2100 | 149.37 | 157.23 | 161.68 | 165.37 | 186.92 | 191.05 |
| | Female | 2101 | 152.55 | 163.79 | 168.83 | 173.21 | 199.59 | 200.33 |
| | Female | 2102 | 154.36 | 168.05 | 169.74 | 177.49 | 195.39 | 201.75 |
| | Female | 2103 | 155.96 | 163.52 | 168.37 | 186.30 | 167.33 | 182.33 |
| | Female | 2104 | 157.83 | 166.18 | 167.35 | 165.29 | 185.83 | 190.86 |
| 1200mg/kg bw | Female | 2200 | 150.23 | - | - | - | - | - |
| | Female | 2201 | 152.76 | 156.63 | 164.88 | 181.32 | 188.74 | 194.31 |
| | Female | 2202 | 155.02 | 157.42 | 160.92 | 150.29 | 171.39 | 180.36 |
| | Female | 2203 | 156.31 | - | - | - | - | - |
| | Female | 2204 | 158.39 | - | - | - | - | - |
| 1600mg/kg bw | Female | 2300 | 150.52 | 142.68 | - | - | - | - |
| | Female | 2301 | 152.95 | 150.47 | 151.92 | 161.18 | 183.94 | 190.86 |
| | Female | 2302 | 155.09 | - | - | - | - | - |
| | Female | 2303 | 156.70 | - | - | - | - | - |
| | Female | 2304 | 158.33 | - | - | - | - | - |
| 2000mg/kg bw | Female | 2400 | 151.54 | - | - | - | - | - |
| | Female | 2401 | 153.27 | - | - | - | - | - |
| | Female | 2402 | 155.24 | - | - | - | - | - |
| | Female | 2403 | 156.87 | - | - | - | - | - |
| | Female | 2404 | 158.96 | 148.37 | 144.56 | 136.33 | 150.45 | 162.33 |
| 2500mg/kg bw | Female | 2500 | 152.33 | - | - | - | - | - |
| | Female | 2501 | 154.04 | - | - | - | - | - |
| | Female | 2502 | 155.38 | - | - | - | - | - |
| | Female | 2503 | 156.92 | - | - | - | - | - |
| | Female | 2504 | 159.07 | - | - | - | - | - |

Note: "-" means that the animal has been dead.

Fig. 8 (cont.)

Attached table 5. Result table of animal gross anatomy

| Animal code | Gender | Death type | Visceral organ | Gross anatomy result |
|---|---|---|---|---|
| 1100 | Male | Planned anatomy | All | No macroscopic abnormality |
| 1101 | Male | Planned anatomy | All | No macroscopic abnormality |
| 1102 | Male | Planned anatomy | All | No macroscopic abnormality |
| 1103 | Male | Planned anatomy | All | No macroscopic abnormality |
| 1104 | Male | Planned anatomy | All | No macroscopic abnormality |
| 1200 | Male | Planned anatomy | All | No macroscopic abnormality |
| 1201 | Male | Planned anatomy | All | No macroscopic abnormality |
| 1202 | Male | Planned anatomy | All | No macroscopic abnormality |
| 1203 | Male | Planned anatomy | All | No macroscopic abnormality |
| 1204 | Male | Planned anatomy | All | No macroscopic abnormality |
| 1300 | Male | Planned anatomy | All | No macroscopic abnormality |
| 1301 | Male | Planned anatomy | All | No macroscopic abnormality |
| 1302 | Male | Planned anatomy | All | No macroscopic abnormality |
| 1303 | Male | Planned anatomy | All | No macroscopic abnormality |
| 1304 | Male | Planned anatomy | All | No macroscopic abnormality |
| 1400 | Male | Planned anatomy | All | No macroscopic abnormality |
| 1401 | Male | Unplanned anatomy | All | No macroscopic abnormality |
| 1402 | Male | Planned anatomy | All | No macroscopic abnormality |
| 1403 | Male | Unplanned anatomy | All | No macroscopic abnormality |
| 1404 | Male | Unplanned anatomy | All | No macroscopic abnormality |
| 1500 | Male | Planned anatomy | All | No macroscopic abnormality |
| 1501 | Male | Planned anatomy | All | No macroscopic abnormality |
| 1502 | Male | Planned anatomy | All | No macroscopic abnormality |
| 1503 | Male | Unplanned anatomy | All | No macroscopic abnormality |
| 1504 | Male | Planned anatomy | All | No macroscopic abnormality |
| 1600 | Male | Unplanned anatomy | All | No macroscopic abnormality |
| 1601 | Male | Planned anatomy | All | No macroscopic abnormality |
| 1602 | Male | Unplanned anatomy | All | No macroscopic abnormality |
| 1603 | Male | Planned anatomy | All | No macroscopic abnormality |
| 1604 | Male | Unplanned anatomy | All | No macroscopic abnormality |
| 1600 | Male | Planned anatomy | All | No macroscopic abnormality |
| 1601 | Male | Unplanned anatomy | All | No macroscopic abnormality |
| 1602 | Male | Unplanned anatomy | All | No macroscopic abnormality |
| 1603 | Male | Unplanned anatomy | All | No macroscopic abnormality |
| 1604 | Male | Unplanned anatomy | All | No macroscopic abnormality |
| 1700 | Male | Unplanned anatomy | All | No macroscopic abnormality |
| 1701 | Male | Unplanned anatomy | All | No macroscopic abnormality |
| 1702 | Male | Unplanned anatomy | All | No macroscopic abnormality |
| 1703 | Male | Unplanned anatomy | All | No macroscopic abnormality |
| 1704 | Male | Unplanned anatomy | All | No macroscopic abnormality |

Fig. 9

Attached table 5. (continued) Result table of animal gross anatomy

| Animal code | Gender | Death type | Visceral organ | Gross anatomy result |
|---|---|---|---|---|
| 2100 | Female | Planned anatomy | All | No macroscopic abnormality |
| 2101 | Female | Planned anatomy | All | No macroscopic abnormality |
| 2102 | Female | Planned anatomy | All | No macroscopic abnormality |
| 2103 | Female | Planned anatomy | All | No macroscopic abnormality |
| 2104 | Female | Planned anatomy | All | No macroscopic abnormality |
| 2200 | Female | Unplanned anatomy | All | No macroscopic abnormality |
| 2201 | Female | Planned anatomy | All | No macroscopic abnormality |
| 2202 | Female | Planned anatomy | All | No macroscopic abnormality |
| 2203 | Female | Unplanned anatomy | All | No macroscopic abnormality |
| 2204 | Female | Unplanned anatomy | All | No macroscopic abnormality |
| 2300 | Female | Unplanned anatomy | All | No macroscopic abnormality |
| 2301 | Female | Planned anatomy | All | No macroscopic abnormality |
| 2302 | Female | Unplanned anatomy | All | No macroscopic abnormality |
| 2303 | Female | Unplanned anatomy | All | No macroscopic abnormality |
| 2304 | Female | Unplanned anatomy | All | No macroscopic abnormality |
| 2400 | Female | Unplanned anatomy | All | No macroscopic abnormality |
| 2401 | Female | Unplanned anatomy | All | No macroscopic abnormality |
| 2402 | Female | Unplanned anatomy | All | No macroscopic abnormality |
| 2403 | Female | Unplanned anatomy | All | No macroscopic abnormality |
| 2404 | Female | Planned anatomy | All | No macroscopic abnormality |
| 2500 | Female | Unplanned anatomy | All | No macroscopic abnormality |
| 2501 | Female | Unplanned anatomy | All | No macroscopic abnormality |
| 2502 | Female | Unplanned anatomy | All | No macroscopic abnormality |
| 2503 | Female | Unplanned anatomy | All | No macroscopic abnormality |
| 2504 | Female | Unplanned anatomy | All | No macroscopic abnormality |

Fig. 9 (cont.)

SELENIUM-ENRICHED TEA POLYPHENOL SELENIDE PREPARATION

CROSS REFERENCE OF RELATED APPLICATION

This is a U.S. National Stage under 35 U.S.C 371 of the International Application PCT/CN2014/074095, filed Mar. 26, 2014, which claims priority under 35 U.S.C. 119(a-d) to CN 201410080979.8, filed Mar. 6, 2014.

BACKGROUND OF THE PRESENT INVENTION

Field of Invention

The present invention relates to an organic selenium compound, and more particularly to a new selenium-enriched nontoxic organic selenium compound, i.e. tea polyphenol selenide, which could be widely applied in fields of health and nutritional products, enriched food, drugs, veterinary drug, etc.

Description of Related Arts

With the development of economy, people's knowledge of health as well as requirement for it have been increasing day by day. However, the amount of diseases caused by environmental deterioration is also rising, which deeply plagues people. Hence, a public awareness of disease prevention and health care has been significantly raised. For example, the number of people taking health products greatly increases in China, America, Japan, Korea, etc. yearly, and a huge market of hundreds of billions of dollars is formed.

Since the beginning of the century, the health product of organic selenium has been in the ascendant. However, limited by its toxicity, the health product of organic selenium in the global market has low selenium content at present. As a result, it has not been given full play, and its outstanding and broad-spectrum effect has not been shown. Therefore, searching for a new type of selenium-enriched nontoxic organic selenium compound has become a hot and difficult research issue.

Tea polyphenol (TP) is a natural organic compound extracted from tea leaves, without any toxicity, side effect or off-flavor. TP is a generic term of polyphenols in tea leaves, comprising: flavanols, anthocyanins, flavone, flavonol, phenolic acids, etc., wherein the flavanols (catechin) is the most important. The flavanols mainly comprising catechin accounts for 60%~80% of the TP, wherein the components with a relatively high content are L-EGCG(50%-60%), L-EGC(15%-20%), L-ECG(10%-15%) and L-EC(5%-10%). TP, also called tea tannin, is one of the main ingredients to form the color, aroma and taste of the tea, and is one of the main ingredients having the healthcare function. TP comprises a lot of phenolic hydroxyl groups in the structure, which are easily oxidized into quinones and generate $H^+$, therefore TP has a strong antioxidant activity. Scavenging free radicals and antioxidation are the most important bioactivity of TP, which are the basis of anticancer pharmacological action.

The molecular formula of TP is $C_{17}H_{19}N_3O$, and the molecular weight is 281.36. The condensed structural formula of TP is:

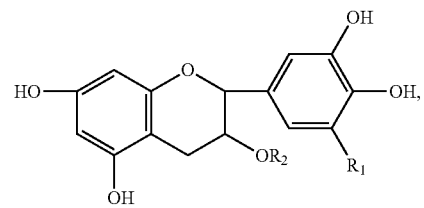

wherein $R_1$=H, or OH, $R_2$=H, or

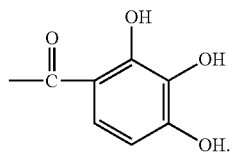

The research on TP has a history of more than one hundred years in the world. According to the long-term research, analysis, and practical application, TP has following functions of:
1) scavenging harmful free radicals,
2) strong antioxidation,
3) anti-aging,
4) anti-radiation,
5) anti-tumor, inhibiting cancer cell,
6) antibacterial, sterilizing, antiviral,
7) anti-atherosclerosis,
8) strengthening heart function,
9) anti-arrhythmia,
10) preventing and curing cerebral ischemia-reperfusion injury,
11) preventing tooth decay and protecting teeth,
12) whitening skin, and reducing wrinkles.

In 2013, only Europe, America, Japan and other countries consumed more than 1200 tons of highly purified TP, which was mainly applied in health food, health care products and drug additives.

As is known to all, selenium is an essential and salubrious element for preventing and curing diseases. It is closely associated with over 40 major diseases, which has been known to the public in developed areas. However, the insiders and outsiders are deeply concerned with how to increase the selenium content in the organic selenium and reduce its toxicity at the same time. Therefore, a new selenium-enriched nontoxic organic selenium compound, i.e. tea polyphenol selenide, was born at the right moment.

SUMMARY OF THE PRESENT INVENTION

An object of the present invention is to provide a selenium-enriched tea polyphenol selenide, having a functional group of alkali metal ion and selenium coordination complex, having a selenium content of 23.4%, so as to increase effects of scavenging free radicals, antioxidation, and anticancer.

Another object of the present invention is to provide a nontoxic tea polyphenol selenide. As the selenium content is increased, toxicity of the tea polyphenol selenide is reduced by means of improved technology, in such a manner that side effects are reduced.

Another object of the present invention is to provide a method for preparing selenium-enriched tea polyphenol selenide.

In order to accomplish the above objects, the present invention provides a selenium-enriched tea polyphenol selenide, having such a structure as:

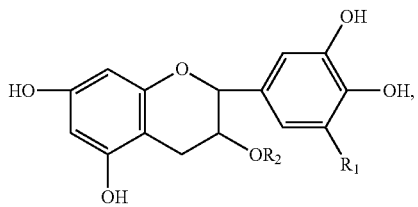

wherein $R_1$ is alkali metal ion and selenium coordination complex, and $R_2$=H, or

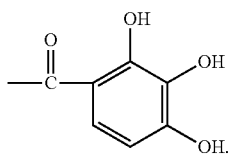

Preferably,

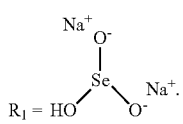

Preferably,

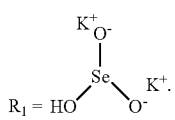

Preferably, the alkali metal ion is magnesium ion.

A method for preparing the selenium-enriched tea polyphenol selenide, comprises:

A) reacting tea polyphenol with at least one inorganic metallic alkali, to obtain tea polyphenol hydroxy acid salt; and B) reacting the tea polyphenol hydroxy acid salt with $SeO_2$, to obtain the selenium-enriched tea polyphenol selenide.

Preferably, a purity of the tea polyphenol in step A) is not less than 98%.

Preferably, in step A), tea polyphenol:inorganic metallic alkali=1:0.1~0.5, a reaction temperature is 70° C.~150° C., and a reaction time is 100 s~250 s.

Preferably, in step B), tea polyphenol hydroxy acid salt: $SeO_2$=1:0.2~0.5, a reaction temperature is 100° C.~250° C., and a reaction time is 80 s~300 s.

Preferably, the inorganic metallic alkali in step A) is sodium hydroxide, potassium hydroxide, or magnesium hydroxide.

The selenium-enriched tea polyphenol selenide prepared by the method in the present invention could be further processed into selenium-enriched tea polyphenol selenide preparations, such as capsule, tablet, granules, oral liquid, and powder, to meet different demands of administration.

The tea polyphenol selenide in the present invention has a high selenium content, and no toxicity, which could be prepared as health and nutritional products, enriched food, drugs, etc.

The mentioned selenium-enriched tea polyphenol selenide could be applied to treating cancer, killing cancer cells, and increasing body immunity.

Benefits of the present invention are as follows. The tea polyphenol selenide in the present invention achieves a high harmony of nontoxicity and high selenium content. Not only is the basic structure of the tea polyphenol preserved, but also the functional group of selenium coordination complex is embedded. The tea polyphenol selenide prepared by this kind of formula and process is a new compound. As a breakthrough, two compounds which have strong functions and a broad spectrum are combined organically. The original biochemical function of the organic selenium is remained, and meanwhile, its characteristics of a high selenium content and no toxicity are strengthened. As a result, the selenium-enriched tea polyphenol selenide has become a new force in fields of health and nutritional products, enriched food, drugs, veterinary drug, etc.

These and other objectives, features, and advantages of the present invention will become apparent from the following detailed description, the accompanying drawings, and the appended claims.

BRIEF DESCRIPTION OF THE DRAWINGS

The patent of application file contains at least one drawing executed in color. Copies of this patent or patent application publication with color drawing(s) will be provided by the Office upon request and payment of the necessary fee.

FIG. 1 is a high performance liquid chromatogram of tea polyphenol selenide having a functional group of alkali metal ion and selenium coordination complex which is obtained according to a preferred embodiment of the present invention;

FIG. 2 is a table of dose design and animal dose groups;

FIG. 3 is a table of concentration of test sample;

FIG. 4 is a table of code of animal anatomized as planned;

FIG. 5 is a result table of clinical symptom;

FIG. 6 is a result table of animal death;

FIG. 7 is a comparison table of animal weight when grouping;

FIG. 8 is a change table of animal weight;

FIG. 9 is a result table of animal gross anatomy.

DETAILED DESCRIPTION OF THE PREFERRED EMBODIMENT

According FIG. 1 of a preferred embodiment of the present invention, a selenium-enriched tea polyphenol selenide having a selenium content of 23.4% is a tea polyphenol hydroxy acid salt having a functional group of alkali metal ion and selenium coordination complex.

A selenium-enriched tea polyphenol selenide, has a structure as:

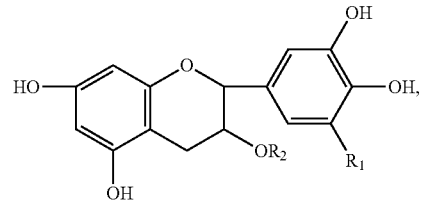

wherein $R_1$ is alkali metal ion and selenium coordination complex, and $R_2$=H, or

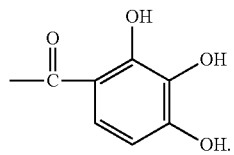

Preferably,

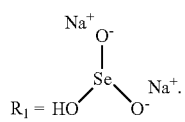

Preferably,

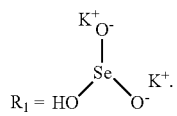

Preferably, the alkali metal ion is magnesium ion.

A method for preparing the selenium-enriched tea polyphenol selenide, comprises:

A) reacting tea polyphenol with at least one inorganic metallic alkali, to obtain tea polyphenol hydroxy acid salt; and B) reacting the tea polyphenol hydroxy acid salt with $SeO_2$, to obtain the selenium-enriched tea polyphenol selenide.

Preferably, a purity of the tea polyphenol in step A) is not less than 98%.

Preferably, in step A), tea polyphenol:inorganic metallic alkali=11:0.1~0.5, a reaction temperature is 70° C.~150° C., and a reaction time is 100 s~250 s.

Preferably, in step B), tea polyphenol hydroxy acid salt:$SeO_2$=1:0.2~0.5, a reaction temperature is 100° C.~250° C., and a reaction time is 80 s~300 s.

Preferably, the inorganic metallic alkali in step A) is sodium hydroxide, potassium hydroxide, or magnesium hydroxide.

The selenium-enriched tea polyphenol selenide prepared by the method in the present invention could be further processed into selenium-enriched tea polyphenol selenide preparations, such as capsule, tablet, granules, oral liquid, and powder, to meet different demands of administration. A method for preparing the tea polyphenol selenide preparation is described as follows.

The method for preparing the tea polyphenol selenide preparation comprises:

A) reacting tea polyphenol with at least one inorganic metallic alkali, to obtain tea polyphenol hydroxy acid salt;

B) reacting the tea polyphenol hydroxy acid salt with $SeO_2$, to obtain the tea polyphenol selenide; and C) processing the tea polyphenol selenide into capsule, tablet, granules, oral liquid, or powder.

The tea polyphenol selenide in the present invention has high selenium content, and no toxicity, which could be prepared as health and nutritional products, enriched food, drugs, etc.

Example 1

A) reacting tea polyphenol of a purity of 98% with sodium hydroxide, to obtain tea polyphenol hydroxy acid sodium, wherein tea polyphenol:sodium hydroxide=1:0.3, a reaction temperature is 100° C., and a reaction time is 150 s; and B) reacting the tea polyphenol hydroxy acid sodium with $SeO_2$, to obtain the selenium-enriched tea polyphenol selenide, wherein tea polyphenol hydroxy acid sodium:$SeO_2$=1:0.4, a reaction temperature is 150° C., and a reaction time is 200 s.

Example 2

A) reacting tea polyphenol of a purity of 98% with potassium hydroxide, to obtain tea polyphenol hydroxy acid potassium, wherein tea polyphenol:potassium hydroxide=1:0.5, a reaction temperature is 130° C., and a reaction time is 200 s; and B) reacting the tea polyphenol hydroxy acid potassium with $SeO_2$, to obtain the selenium-enriched tea polyphenol selenide, wherein tea polyphenol hydroxy acid potassium:$SeO_2$=1:0.5, a reaction temperature is 200° C., and a reaction time is 280 s.

Example 3

A) reacting tea polyphenol of a purity of 99% with magnesium hydroxide, to obtain tea polyphenol hydroxy acid magnesium, wherein tea polyphenol:magnesium hydroxide=1:0.2, a reaction temperature is 80° C., and a reaction time is 120 s; and B) reacting the tea polyphenol hydroxy acid magnesium with $SeO_2$, to obtain the selenium-enriched tea polyphenol selenide, wherein tea polyphenol hydroxy acid magnesium:$SeO_2$=1:0.3, a reaction temperature is 100° C., and a reaction time is 100 s.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

An acute oral toxicity testing of P1 in rats is described as follows, wherein P1 is tea polyphenol selenide obtained according to the embodiment 1 of the present invention.

Abstract of Toxicity Testing

Objective: Observing toxic reactions and death of rats after intragastric administration of test sample P1 in them, in order to preliminarily evaluate the safety of the test sample P1

Method: 50 healthy SD rats, selected as the test animals, half male and half female, were randomly divided into 5 groups, i.e., dose group 1 (1000 mg/kg), dose group 2 (1280 mg/kg), dose group 3 (1600 mg/kg), dose group 4 (2000 mg/kg), dose group 5 (2500 mg/kg). Each dose group had 10 animals, half male and half female. Then 3 more dose groups were added, i.e. 3000 mg/kg, 4000 mg/kg, and 4500 mg/kg, each of the dose groups had 5 male rats. The night before the dosing day, the rats were not allowed to eat, but allowed to drink. On the dosing day, the rats were intragastrically fed with 1 ml/100 g bw once. Within 4 hours after the intragastric administration, reactions and death of the animals were closely observed. Then the animals were observed twice a day, morning and afternoon, for 14 days to record the status of death and near-death. The death animals were necropsied promptly. Other animals were processed by gross anatomy after the end of the observation period, and the gross pathologic change of each animal was recorded.

Result: (1) After the rats were fed with P1 and during the observation period, all of 5 female rats in the dose group 5 died, and 1 male rat in the dose group 5 died. In the dose group 4, 3 male rats died and 4 female rats died. In the dose group 3, no male rat died and 4 female rats died. In the dose group 2, no male rat died and 3 female rats died. In the dose group 1, no male rat died and no female rat died. In the dose group of 3000 mg/kg, 3 male rats died. In the dose group of 4000 mg/kg, 4 male rats died. In the dose group of 4500 mg/kg, 5 male rats died. (2) The animals were necropsied after the observation period of 14 days, and no abnormality was found.

Conclusion: According to [H] GPT1-1 Technical guidelines for acute toxicity testing of chemicals issued by China Food and Drug Administration (CFDA) and results of pre-test, the doses were designed and the test were processed. According to the results of the test, median lethal dose ($LD_{50}$) of P1 in this acute oral toxicity testing in male and female SD rats is calculated and listed as follows.

Male rats: 2648.4 mg/kg, confidence limit: 2143.4-3338.4 mg/kg

Female rats: 1365.9 mg/kg, confidence limit: 1037.5-1662.8 mg/kg

1. Name of the testing
    Acute oral toxicity testing of P1 in rats
2. Objective of the testing
    Researching median lethal dose ($LD_{50}$) of P1 in acute oral toxicity testing in rats, and providing basis for dose design in subchronic and chronic toxicology research
3. Criterion and reference
    The testing is based on [H] GPT1-1 Technical guidelines for acute toxicity testing of chemicals issued by China Food and Drug Administration (CFDA).
4. Testing institution
    Testing institution: Shanghai Siper-BK Lab Animal Co. Ltd.
    Address: 3577 Jinke Rd., Pudong New District, Shanghai
    Postcode: 201203
    Telephone: 021-50793648
    Fax: (021) 50793645
5. Client and contact person
    Client: Shanghai Spark Pharmaceutical Co., Ltd. (Shanghai Ai Qi Yi Yao Ji Shu You Xian Gong Si)
    Address: Rm. 1110, No. 781, Cailun Rd., Zhangjiang Hi-Tech Park, Shanghai
    Contact person: Diwei Song
    Mobile: 13386238676
6. Principal of testing institution, principal of project and related personnel of testing
    Principal of testing institution: Guoqiang Chen

| Address: 3577 Jinke Rd. | Postcode: 201203 |
| Telephone: 50793648 | Email: chenguoqiang@slarc.org.cn |

Principal of project: Wei Li

| Address: 3577 Jinke Rd. | Postcode: 201203 |
| Telephone: 50793648 | Email: zhaoliya@slarc.org.cn |

Principal of rearing management: Yi Jin

| Address: 3577 Jinke Rd. | Postcode: 201203 |
| Telephone: 50793648 | Email: jinyi@slarc.org.cn |

Principal of test sample management: Xiaojun Zhu

| Telephone: 50793648 | Email: zhuxiaojun@slarc.org.cn |

Principal of file management: Zhenyu Nan

| Telephone: 50793648 | Email: nanzhenyu@slarc.org.cn |

Symptom observer: Wei Li, Yikai Shi, Lei Liu, etc.
7. Quality assurance
    Principle of QAU: Ying Zhao

| Address: 3577 Jinke Rd. | Postcode: 201203 |
| Telephone: 50793648 | Email: zhaoying@slarc.org.cn |

8. Test sample and solvent
    8.1 Test sample
        Chinese name: P1
        English name: P1
        Lot number: 20130903
        CAS number: Not provided by client
        Physical property: Solid powder
        Purity: Not provided by the client
        Provider: Shanghai Spark Pharmaceutical Co., Ltd. (Shanghai Ai Qi Yi Yao Ji Shu You Xian Gong Si)
        Providing date: 20130903
        Expiry date: 20150903
        Total weight: (Including the container weight) 112.9723 g
        Protective measure: The persons who contact with the test sample should take appropriate protective measures, including masks, hats, gloves, overalls, and etc.
        Storage condition: At room temperature
        Storage site: Test sample room of the testing institution
        Stability: The client confirmed that the test sample was stable at the storage temperature.
        Treatment of residual test sample: After the testing, residual test sample was taken back to the test sample room, and treated according to SOP.
    8.2 Solvent
        Name: ultrapure water
9. Test schedule
    Date of initial test: Sep. 11, 2013
    Date of introducing the rats: Sep. 13, 2013

Date of starting the test: Sep. 26, 2013
Date of ending the test: Dec. 22, 2013
Date of draft report: Jan. 6, 2014
Date of final report: Jan. 9, 2014

10. Material and method 10.1 Test system

Species: Rat

Strain: SD (Sprague Dawley)

Level: SPF, referring to National Standard of People's Republic of China—GB 14922.2-2011 Experimental Animal Microbiology Level Monitoring Provider: Shanghai Sippr-BK Lab Animal Co. Ltd.

Experimental animal production license: SCXK(Shanghai)2008-0016, SCXK(Shanghai)2013-0016

Experimental animal quality certification: 2008001634761, 2008001635380, 2008001636435

Choosing reason: The rat is recognized as the preferred animal for this kind of acute toxicity testing. It has stable hereditary feature and distinct background data.

Requirement of animals: Virgin, healthy, and compliant with quality requirements on experimental animals Animal count: total 80, female 27, male 53; used 65, female 25, male 40

Weight: At the time of introducing, male animals' weight range 110-130 g, female animals' weight range 130-150 g Health examination and adaptation: Within 24 hours after the animals were introduced, the animals were checked-up, no abnormality was found. During the adaptation period, each cage contained 5 animals, which adapted for 7-13 days.

10.2 Test condition

Rearing condition: The test site is located at layer 1, layer 2, layer 3, layer 4, and layer 5 of the rearing rack 2008042-ZYZX in Room 3139, barrier system, No. 3 building of the testing institution. The experimental animal usage licenses are SYXK(Shanghai)2008-0058 and SYXK(Shanghai)2013-0058. Testing animals were raised in plastic cages. During the adaptation period, the animals were raised in cages having size of L38.00 cm*W32.5 cm*H17.5 cm, which were put on the rearing rack. The rearing rack has 7 layers, each of which comprises 6 cages. The rearing rack has a size of L167.0 cm*W70.0*H171.0 cm. After dosing, each cage contained 5 animals.

The floor of the animal room was wiped with disinfectant every day, and the disinfectant was replaced every week. The cages were replaced once a week. Water was fed with plastic bottles, and the animals drank and ate freely.

Environmental condition: The air pressure in the animal room (L6.2 m*W5.8 m*H2.7 m) was kept positive by an air conditioning unit, which took in the fresh air and exhausted air. The temperature was 20-26° C. The relative humidity was 40-70%, except when the room was being cleaned. The illumination was not less than 200 Lux, and the illumination was on for 12 hours and off for 12 hours a day. The noise was not more than 60 dB. Ventilation frequency was not less than 15 times per hour. The falling bacterial count was not more than 3. (When there was no animal, a plate with a diameter of 9 cm was exposed for 30 minutes.)

Ingestion and drinking: The animal fodder was the complete nutritional solid fodder, which was provided by Shanghai Sippr-BK Lab Animal Co. Ltd. The fodder was sterilized with high pressure steam before eaten by the experimental animals. The fodder quality testing report was provided, which proved that both the nutritional ingredient and the pollutant content conformed to national standard GB14924.3-2010 Nutritional ingredient of compound feed for experimental animal.

The water the animals drunk was the filtered water prepared by the water purification system of the testing institution. The water quality was tested by Shanghai Pony Testing Technology Co., Ltd, and the test indexes conformed to GB 5749-2006 Hygienic standard for drinking water.

Animal welfare: The residual animals after grouping were used in other testings or euthanized. The animals near death in the testing or alive at the end of the testing were euthanized. The euthanasia was embodied as carbon dioxide suffocation. The corpses were disposed by Shanghai Animal Harmless Disposal Center.

10.3 Test method 10.3.1 Dose design 5 dose groups were designed, i.e., dose group 1 (1000 mg/kg), dose group 2 (1280 mg/kg), dose group 3 (1600 mg/kg), dose group 4 (2000 mg/kg), dose group 5 (2500 mg/kg). Then 3 more dose groups were added, i.e. 3000 mg/kg, 4000 mg/kg, and 4500 mg/kg. The animals were intragastrically fed with test sample suspension of 26 mg/mL, 43.2 mg/mL, 72 mg/mL, 120 mg/mL, 200 mg/mL, 250 mg/mL, 300 mg/mL, 400 mg/mL, and 450 mg/mL, respectively. The intragastric volume is 1 ml/100 g bw, and the animals were exposed once.

The dose was designed based on [H] GPT1-1 Technical guidelines for acute toxicity testing of chemicals issued by China Food and Drug Administration (CFDA) and results of the pre-test. In the pre-test, 2 female animals and 2 male animals were orally exposed to the test sample of each dose. The results indicated that all of the 4 animals exposed to the test sample of 2500 mg/kg died; 1 of the animals exposed to the test sample of 2000 mg/kg died; none of the 4 animals exposed to the test sample of 1000 mg/kg died; and none of the 4 animals exposed to the test sample of 200 mg/kg died. Therefore, 5 doses between 1000 mg/kg and 2500 mg/kg were designed for the formal test. Afterwards, 3 more dose groups were added, i.e. 3000 mg/kg, 4000 mg/kg, and 4500 mg/kg, because not all of the male rats died from the high dose.

10.3.2 Grouping animals

The animals were divided into groups after the end of the adaptation period.

Grouping method: After the end of the adaptation period, all of the animals were weighed and their average weight was calculated. The animals usually in good condition were selected. The weight difference among the animals of the same gender and in the same dose group was less than 10% of the average weight. The difference of the average weights of the animals of the same gender between any two dose groups was less than 5%. The animals were identified by original codes. The animals were ranked from largest weight to smallest weight, and were divided into groups, wherein each group comprised 5 animals. From each of the five groups, one animal was randomly taken out to form a certain dose group. New codes of the animals were recorded, and they were random and not ranked in ascending or descending order of the weight. The animals were taken out according to original codes. The corresponding dose groups and new codes were found in the grouping table, and then the animals were put into the corresponding dose groups in turn.

Animal identification: The animals were identified by cage cards, picric acid hair dye, and ear tag. The cage card showed the code and the dose group of the animal. The hair identification showed the units digit of the animal code in one group, i.e. 0-9. The ear tag showed the units digit of the animal code in one group, i.e. 0-9, and the group number. The dose design and animal dose groups are shown in FIG. 2.

10.3.3 Preparation of test sample

The scale 40 mL or 10 mL was calibrated on the reagent bottle with pure water for standby application.

Referring to FIG. 3, the test sample was prepared on the day before the dosing day. The theoretical sample weights were calculated according to the dose design, and the test samples were respectively weighed out and put into the calibrated reagent bottles. Little ultrapure water was added and stirred evenly, and then the volume of the solution was adjusted to the calibrated scale. After the preparation, the reagent bottles were labeled for standby application. The calculating formulas are as follows. Concentration of test sample (mg/mL)=Dose (mg/kg)/Intragastric volume (mL/kg). Theoretical sample weight (mg)=Preparation volume (mL)*Concentration of test sample (mg/mL).

10.3.4 Exposure routes, exposure cycle, and observation period

Based on the probable routes through which human beings may be exposed to the test sample, the animals were orally exposed to the test sample by intragastric administration. The prepared test sample was stirred with a magnetic stirring rod for 5 minutes, and then the dosing was started. The test sample was being stirred during the dosing. The dosing volume is equal to 10 mL/kg*weight. Before the dosing, the animals were weighed, and the dosing volume is calculated. The intragastric administration was processed with disposable sterile syringes having range of 5 mL, minimum scale of 0.2 mL, and syringe needle of 16 G. The animals were dosed with test sample suspension of certain concentration. The animals were dosed at the grouping day. The night before the dosing day, the animals were not allowed to eat, but allowed to drink. 2 hours after the intragastric administration, the animals resumed feeding. The animals were exposed to the test sample once. The observation period lasted for 14 days. When all symptoms disappeared, the test ended. When the test ended, the animals in dose group 1, dose group 2, dose group 3, dose group 4, dose group 5, dose group 6 and dose group 7, were processed with gross anatomy according to the codes of animals anatomized as planned after exposure (shown in FIG. 4).

10.3.5 Clinical observation and examination

1) Symptoms observation

Within 4 hours after the dosing, the animals were closely observed. From the $1^{st}$ day to the $14^{th}$ day after the dosing, the animals were observed once a day to record symptoms, wherein the dosing day was the $0^{th}$ day. The animals were observed to record the changes of skin and hair, eyes, mucous membranes, respiratory system, circulatory system and nervous system, especially the changes of physical activity and behavior. Toxic symptoms of the animals, and its occurrence, remission and disappearance time were recorded. When the animals died, the death time was recorded.

The animals were observed twice a day, morning and afternoon, to record the number of death and near-death.

2) Weighing

The animals were weighed on the dosing day and when they died. During the observation period, the animals were weighed once every 3 days.

3) Gross anatomy

All animals should be processed with gross anatomy. During the test, the animals executed because of near-death and dead animals were processed with gross anatomy promptly. Other animals were executed and processed with gross anatomy after the end of the observation period. The gross pathologic change of each animal was recorded.

10.4 Data processing 10.4.1 Statistically calculating $LD_{50}$ and confidence limit with bliss software 11. Result and conclusion 11.1 Result 11.1.1 Result of clinical observation Clinical symptoms of the 8 dose groups are shown in FIG. 5.

11.1.2 Statistical result of animal death

During the observation period, all of the 5 female rats in the dose group 5 died, and 1 of male rats in the dose group 5 died. In the dose group 4, 3 male rats died and 4 female rats died. In the dose group 3, no male rat died and 4 female rats died. In the dose group 2, no male rat died and 3 female rats died. In the dose group 1, no male rat died and no female rat died. In the dose group of 3000 mg/kg, 3 male rats died. In the dose group of 4000 mg/kg, 4 male rats died. In the dose group of 4500 mg/kg, 5 male rats died, as shown in FIG. 6.

11.1.3 Animal weight

The animals were weighed on the dosing day and when they died. During the observation period, the animals were weighed once every 3 days, as shown in FIGS. 7-8.

11.1.4 Result of gross anatomy

The test animals were processed with gross anatomy, and no abnormality was found, as shown in FIG. 9.

11.2 Conclusion 11.2.1 $LD_{50}$ and confidence limit of the test sample

According to [H] GPT1-1 Technical guidelines for acute toxicity testing of chemicals issued by China Food and Drug Administration (CFDA) and results of pre-test, doses were designed and the test were processed. According to the results of the test, median lethal dose ($LD_{50}$) of P1 in this acute oral toxicity testing in male and female SD ratsis calculated and listed as follows.

Male rats: 2648.4 mg/kg, confidence limit: 2143.4-3338.4 mg/kg

Female rats: 1365.9 mg/kg, confidence limit: 1037.5-1662.8 mg/kg

12. File storage

---

Principal of file management: Zhenyu Nan    Telephone: 50793648

---

After being archived, the following files will be preserved in the archives office of the test institution for 10 years.
Test plan and its revised sheets
original record
Final report, etc.

What is claimed is:

1. A tea polyphenol selenide, having a structure as:

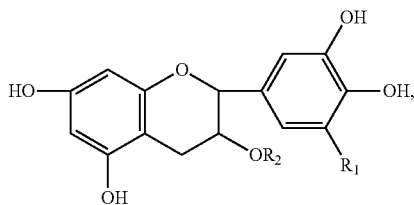

wherein

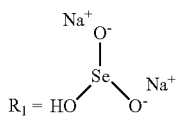

or

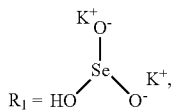

and $R_2$=H, or

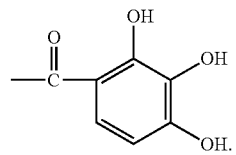

2. A method for preparing the tea polyphenol selenide, as recited in claim 1, comprising:
   A) reacting tea polyphenol with at least one inorganic metallic alkali, to obtain tea polyphenol hydroxy salt; and
   B) reacting the tea polyphenol hydroxy salt with $SeO_2$, to obtain the tea polyphenol selenide.

3. The method for preparing the tea polyphenol selenide, as recited in claim 2, wherein the purity of the tea polyphenol in step A) is not less than 98%.

4. The method for preparing the tea polyphenol selenide, as recited in claim 2, wherein in step A), tea polyphenol: inorganic metallic alkali=1:0.1 to 1:0.5, a reaction temperature is 70° C. to 150° C., and a reaction time is 100 s to 250 s.

5. The method for preparing the tea polyphenol selenide, as recited in claim 2, wherein in step B), tea polyphenol hydroxy salt: $SeO_2$=1:0.2 to 1:0.5, a reaction temperature is 100° C. to 250° C., and a reaction time is 80 s to 300 s.

6. The method for preparing the tea polyphenol selenide, as recited in claim 2, wherein the inorganic metallic alkali in step A) is sodium hydroxide, potassium hydroxide, or magnesium hydroxide.

7. A method for preparing preparation of tea polyphenol selenide, as recited in claim 1, comprises:
   A) reacting tea polyphenol with at least one inorganic metallic alkali, to obtain tea polyphenol hydroxy salt;
   B) reacting the tea polyphenol hydroxy salt with $SeO_2$, to obtain the tea polyphenol selenide; and
   C) further preparing the tea polyphenol selenide into capsule, tablet, granules, oral liquid, or powder.

8. A health and nutritional product, enriched food or drug, comprising the tea polyphenol selenide, as recited in claim 1.

* * * * *